(12) United States Patent
Huang et al.

(10) Patent No.: US 7,774,212 B2
(45) Date of Patent: Aug. 10, 2010

(54) SYSTEMS AND METHODS FOR DYNAMICALLY DETERMINING DATA-IDENTITY INFORMATION

(75) Inventors: Qingfeng Huang, San Jose, CA (US); James E. Reich, San Francisco, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 773 days.

(21) Appl. No.: 11/504,465

(22) Filed: Aug. 15, 2006

(65) Prior Publication Data

US 2008/0046291 A1 Feb. 21, 2008

(51) Int. Cl.
*G06Q 10/00* (2006.01)
*G06Q 50/00* (2006.01)
(52) U.S. Cl. ........................................................ 705/2
(58) Field of Classification Search .................... 705/2, 705/3; 706/1–9; 707/5
See application file for complete search history.

(56) References Cited

U.S. PATENT DOCUMENTS

| | | | | |
|---|---|---|---|---|
| 4,366,873 A * | 1/1983 | Levy et al. | ............... | 177/25.19 |
| 4,839,824 A * | 6/1989 | Ando | ......................... | 702/166 |
| 4,844,187 A * | 7/1989 | Jabero | ........................... | 177/5 |
| 6,081,619 A * | 6/2000 | Hashimoto et al. | .......... | 382/181 |
| 6,621,013 B2 * | 9/2003 | Tanida et al. | ................... | 177/4 |
| 6,954,148 B2 * | 10/2005 | Pulkkinen et al. | ........ | 340/572.1 |
| 7,001,334 B2 * | 2/2006 | Reed et al. | ................... | 600/300 |
| 7,351,975 B2 * | 4/2008 | Brady et al. | ................. | 250/342 |

OTHER PUBLICATIONS

Farquharson, S.; Lee, Y.; Rainey, P., "A Smart Toilet: Astronaut Health Monitoring by Real-Time Chemical Analysis of Urine", Abstract in Life Support & Biosphere Science Abstracts, v. 7, n. 1 (Abs 63-121), 2000, <http://www.cognizantcommunication.com/filecabinet/Life_Support/Isbs71abs2.html#Isbs71107>.
Conair Corp. "Memory Precision Electronic Scale Model WW60X Product Description", <http:www.conair.com/memory-precision-electronic-scale-p-245-2_60_38.html>.
Crossbow Technology, Inc., "Crossbow Solutions Newsletter", v. 9, First Quarter 2006.

* cited by examiner

*Primary Examiner*—Gerald J. O'Connor
*Assistant Examiner*—Mark Holcomb
(74) *Attorney, Agent, or Firm*—Park, Vaughan & Fleming LLP

(57) ABSTRACT

Techniques are presented for determining threshold probability or confidence levels for associating various types of health information with a set of users. Spatio-temporal information associated with one or more of the subjects is determined. Health information associated with spatial-temporal information is also determined. Candidate health-subject associations are associated with probabilities based on the spatio-temporally tagged identity and spatio-temporally tagged health information. Candidate health-subject associations with probabilities exceeding a threshold probability level are assigned as actual health-subject associations. Treatment plans, reports, remedial procedures and or other health related tests, procedures or the like are determined based on the associated health information.

21 Claims, 9 Drawing Sheets

| SENSOR IDENTIFIER | LOCATION | TIME (UTC) | SENSOR DESCRIPTION |
|---|---|---|---|
| AB36 | BEDROOM | 10:40 | OCCUPANCY |
| AB50 | HALLWAY1 | 10:41 | SOUND |
| AB51 | BATHROOM | 10:42 | HEIGHT |
| AB52 | BATHROOM | 10:42 | SOUND |
| AB50 | HALLWAY1 | 10:48 | SOUND |
| AB54 | KITCHEN | 10:48 | CAMERA |
| AB55 | LIVING ROOM | 10:49 | CAMERA |
| AB56 | FRONT DOOR | 11:15 | ELECTRONIC KEY |
| AB57 | BATHROOM | 11:16 | SCALE |
| AB58 | FRONT DOOR | 11:15 | PRESSURE MAT |
| . | . | . | . |
| . | . | . | . |
| AB77 | LIVING ROOM | 10:00 | CAMERA |

Fig. 4

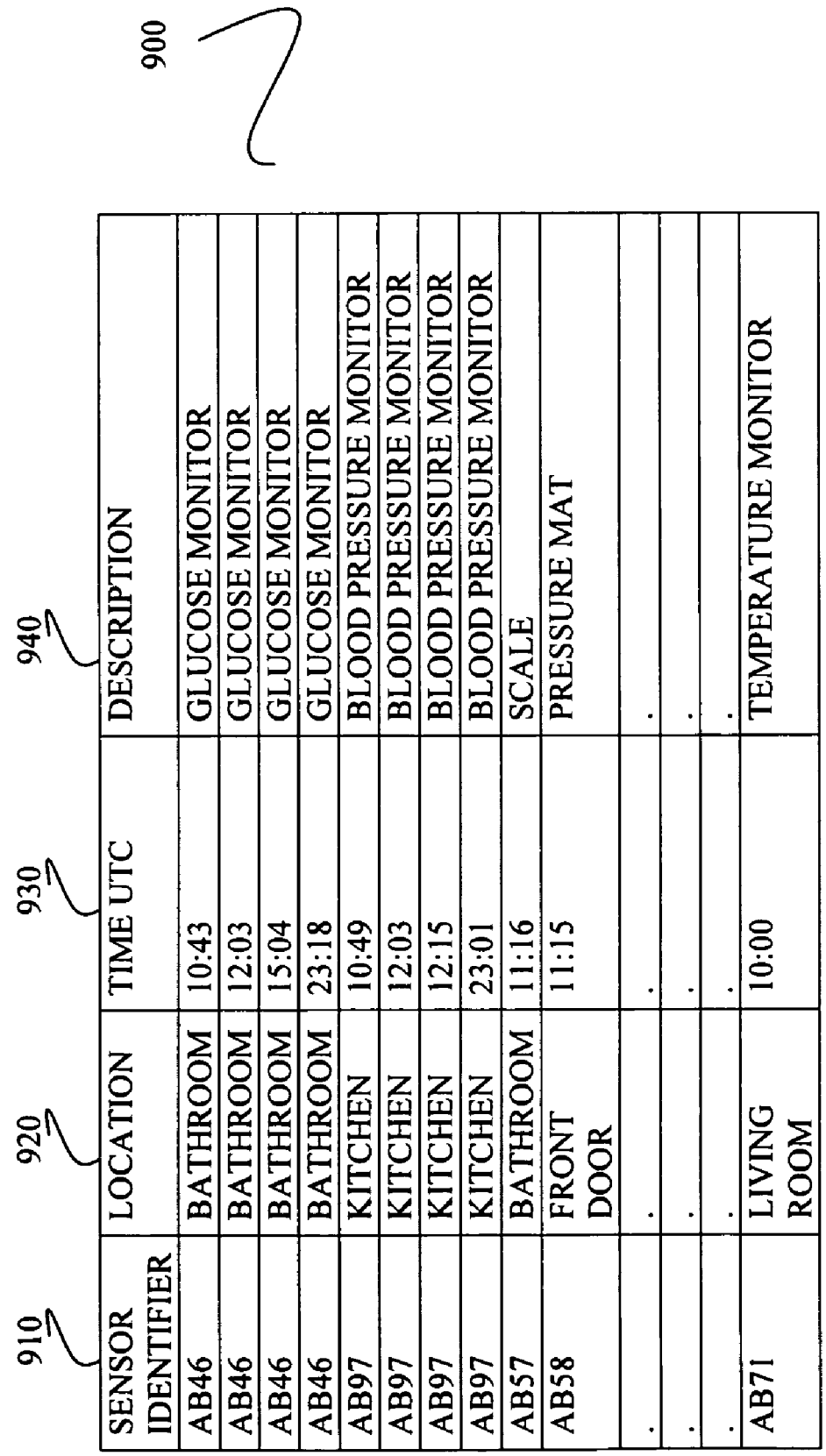

Fig. 5

| SENSOR IDENTIFIER | LOCATION | TIME UTC | DESCRIPTION |
|---|---|---|---|
| AB46 | BATHROOM | 10:43 | GLUCOSE MONITOR |
| AB46 | BATHROOM | 12:03 | GLUCOSE MONITOR |
| AB46 | BATHROOM | 15:04 | GLUCOSE MONITOR |
| AB46 | BATHROOM | 23:18 | GLUCOSE MONITOR |
| AB97 | KITCHEN | 10:49 | BLOOD PRESSURE MONITOR |
| AB97 | KITCHEN | 12:03 | BLOOD PRESSURE MONITOR |
| AB97 | KITCHEN | 12:15 | BLOOD PRESSURE MONITOR |
| AB97 | KITCHEN | 23:01 | BLOOD PRESSURE MONITOR |
| AB57 | BATHROOM | 11:16 | SCALE |
| AB58 | FRONT DOOR | 11:15 | PRESSURE MAT |
| . | . | . | . |
| . | . | . | . |
| AB71 | LIVING ROOM | 10:00 | TEMPERATURE MONITOR |

| SENSOR IDENTIFIER | TIME (UTC) | READING |
|---|---|---|
| AB46 | 10:43 | 10 |
| AB46 | 12:03 | 15 |
| AB46 | 15:04 | 12 |
| AB46 | 23:18 | 13 |
| AB97 | 10:48 | 180/90 |
| AB97 | 12:03 | 180/92 |
| AB97 | 12:15 | 110/90 |
| AB97 | 23:01 | 110/90 |
| AB57 | 11:16 | 160 |
| AB58 | 11:15 | 105 |
| . | . | . |
| . | . | . |
| . | . | . |
| AB71 | 10:00 | 98.9 |

Fig. 6

| SENSOR IDENTIFIER | TIME (UTC) | READING |
|---|---|---|
| AB36 | 10:40 | OCCUPANCY=>TRUE |
| AB50 | 10:41 | GAIT=>USER[1] |
| AB51 | 10:42 | HEIGHT=>USER[1] |
| AB52 | 10:42 | OCCUPANCY=>TRUE |
| AB50 | 10:48 | GAIT=>USER[1] |
| AB54 | 10:48 | OUTLINE=>USER[1] |
| AB55 | 10:49 | OUTLINE=>USER[1] |
| AB56 | 11:15 | EXIT CODE=>USER[1] |
| AB57 | 11:16 | WEIGHT=>USER[2] |
| AB58 | 11:15 | WEIGHT=>USER[1] |
| . | . | |
| . | . | |
| . | . | |
| AB77 | 10:00 | OUTLINE=>USER[7] |

Fig. 7

| USER CHARACTERISTICS |
|---|
| user[1].height=6; |
| user[1].weight=160; |
| user[1].sound.gait=ftp://ftp.abc.com/gait.dat; |
| user[1].sound.voice=ftp://ftp.abc.com/voice.dat; |
| user[1].video.top=ftp://ftp.abc.com/video_top.dat; |
| user[1].video.left=ftp://ftp.abc.com/video_left.dat; |
| user[1].video.right=ftp://ftp.abc.com/video_right.dat; |
| user[1].health.glucose=100; |
| user[1].health.temperature=98.6; |
| . |
| . |
| . |
| user[2].height=5.5; |
| user[2].weight=105; |

| USER CHARACTERISTICS | 1310 |
|---|---|
| user[1].height.variance.value=1; |
| user[1].height.variance.interval=30; |
| user[1].weight.variance.value=1; |
| user[1].weight.variance.interval=30; |
| . |
| . |
| . |
| user[2].height.variance.value=0.5; |
| user[2].height.variance.interval=30; |

SYSTEMS AND METHODS FOR DYNAMICALLY DETERMINING DATA-IDENTITY INFORMATION

BACKGROUND OF THE INVENTION

1. Field of Invention

This invention relates to information retrieval.

2. Description of Related Art

Conventional health monitoring systems provide detailed information about blood pressure, weight, pulse rate, blood pressure and the like. The information from these systems is accumulated and or dynamically downloaded for further analysis. Typically, these devices are permanently or dynamically associated with a specific subject or user. For example, conventional blood pressure monitors such as the CVS blood pressure monitor, allow a number of subjects to record their historical blood pressure information into system memory by manually specifying their identity each time they use the device. One drawback of these systems is that the information is isolated within the device. The user must write down the information to manually create reports for health providers. Some conventional health device manufacturers have addressed these problems by providing interfaces that allow the devices to be accessed over a communications link. For example, the CVS blood pressure monitor offers a module to connect the blood pressure device to a computer. Once uploaded to the computer, the health information is more easily shared with the health provider.

Although useful, these communication-enabled health devices require explicit indications of association between the user and the corresponding health device. These conventional health devices are also difficult to share among multiple users or members of a typical household. This increases the costs associated with gathering and using the information in health related tasks.

SUMMARY OF THE INVENTION

Thus, systems and methods for dynamically determining data-identity association information would be useful. The systems and methods according to this invention provide for determining threshold probability or confidence levels for associating various types of health information with a set of users. Spatio-temporal information associated with one or more of the subjects is determined. Health information associated with spatio temporal information is also determined. Candidate health-subject associations are associated with probabilities based on the spatio-temporally tagged identity and spatio-temporally tagged health information. Candidate health-subject associations with probabilities exceeding a threshold probability level are assigned as actual health-subject associations. Treatment plans, reports, remedial procedures and or other health related tests, procedures or the like are determined based on the associated health information.

BRIEF DESCRIPTION OF THE DRAWINGS

FIG. 4 is an exemplary data structure for storing spatio-temporal subject information according to an aspect of this invention;

FIG. 5 is an exemplary data structure for storing spatio-temporal health information according to an aspect of this invention;

FIG. 6 is an exemplary data structure for storing historical sensor information according to an aspect of this invention;

FIG. 7 is an exemplary data structure for storing historical subject location information according to an aspect of this invention;

FIG. 8 is an exemplary data structure for storing user information according to an aspect of this invention; and FIG. 9 is an exemplary data structure for storing variance models according to an aspect of this invention.

DETAILED DESCRIPTION OF EXEMPLARY EMBODIMENTS

Figure 1:
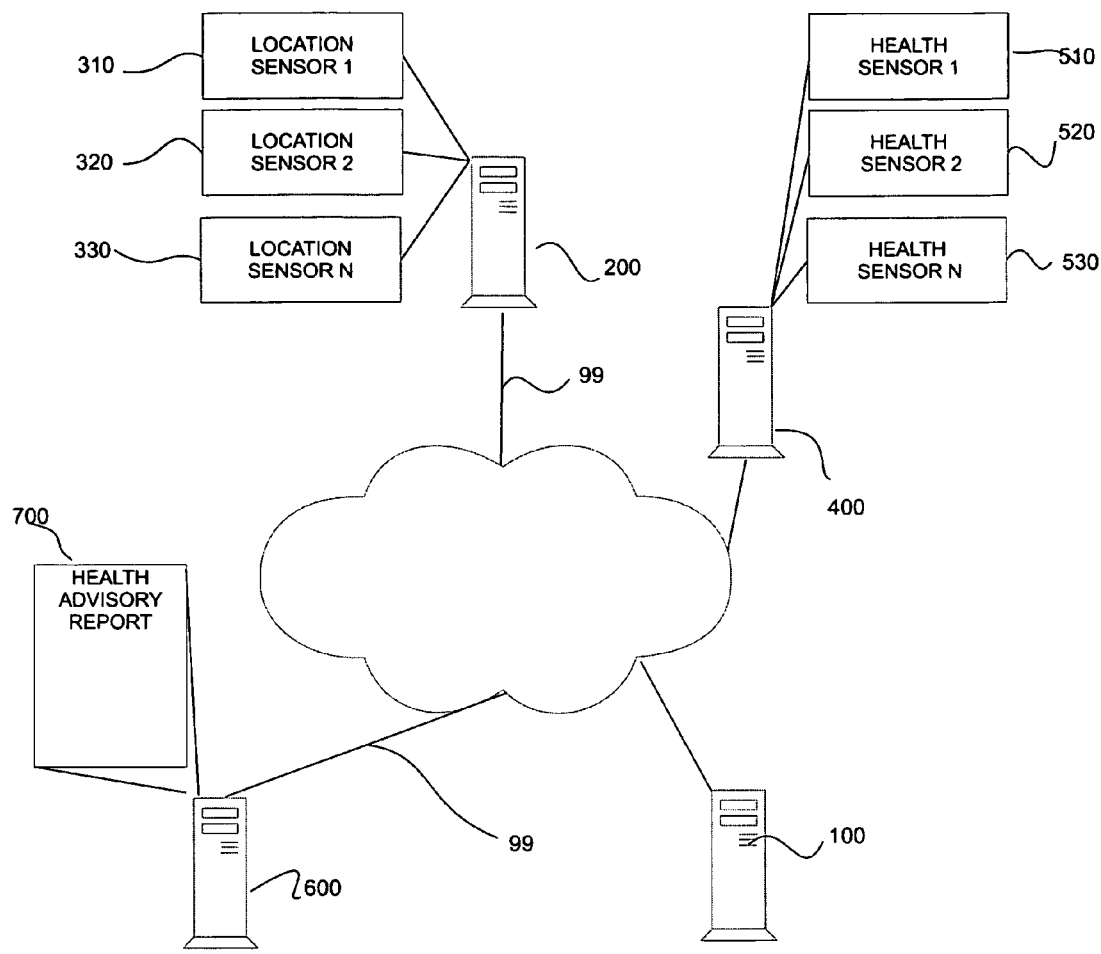
FIG. 1 shows an exemplary overview of a system for dynamically determining data-identity associations according to this invention.

FIG. 1 shows an exemplary overview of a system for dynamically determining data-identity associations 100 according to this invention. The system for dynamically determining data-identity associations 100 is connected via communications links 99 to a location/identity server 200, a health information server 400 and to a health monitoring server 600.

The location/identity server 200 receives location and identity information from a group of location and identity sensors 1-N, 310-330. The health information server 400 receives health information from the health sensors 1-N, 510-530. In one exemplary embodiment, the location/identity server 200 infers the path or trajectory of individual users through a defined or monitored area based on the spatio-temporally tagged sensor information. For example, triggered occupancy sensors in the monitored area are associated with one or more candidate users known to the system. However, some monitored events such as entry or exit from the monitored area with personal key code may be used to uniquely identity a user's trajectory or path. However, it will be apparent that RFID, biometric identification and/or various other methods for identifying a user may also be used in the practice of this invention. In the event of multiple users, the location/identity server 200 may differentiate between multiple users by combining sensor information.

The health server 400 tabulates the spatio-temporally tagged health information derived from the health sensors 1-N, 510-530 over time. The system for dynamically determining data-identity associations 100 associates health information with specific users by correlating the spatio-temporal tagged health information with the spatio-temporal tagged identity information. For example, in one exemplary embodiment, the weight of the user on a monitored bathroom scale is compared to historical weight reading information. Although the user's weight may change or deviate from a norm over time, the individual changes from a prior value are likely to lie within a fairly narrow range indicated by the variance model. The identity of the user may be determined to the extent that each user maintains a different weight. In the case of any ambiguity, information from additional sensors is used. The variance model may also include the effects created by calibration uncertainties among sensors or measurement-to-measurement variation for a particular sensor.

The system for dynamically determining data-identity associations 100 maintains historical information about a user's path or trajectory around the monitored area. Initially-ambiguous health readings may be disambiguated over time as additional inferences are made about the identity of the user. In some embodiments, dynamic incremental feedback is provided to update the scoring model used to determine associations between the spatio-temporally tagged health and subject information. The health-subject information is stored and/or made available to a health monitoring server 600. The health monitoring system 600 analyzes the health-subject information to generate reports, advisories, suggest treatment plans and/or create other procedures or processes.

In another exemplary embodiment according to this invention, the monitored area is an airport. The system for dynamically determining data-identity associations 100 accumulates spatio-temporally tagged readings from temperature, health and/or other sensors for passengers or visitors to the airport. The spatio-temporally tagged health information from the remote temperature sensors and/or other health sensors and the spatio-temporally tagged identity information from a passport and/or identity management system are used to create scored candidate health-subject associations.

The subjects with scores exceeding a predetermined threshold are explicitly associated with the health information. The health information is used to quickly facilitate the screening of airline passengers for flu and the like. Similarly, in spacecraft, hospitals and/or other monitored areas, the system for dynamically determining data-identity associations 100 facilitates accurate reporting of dynamically determined health information.

Figure 2:
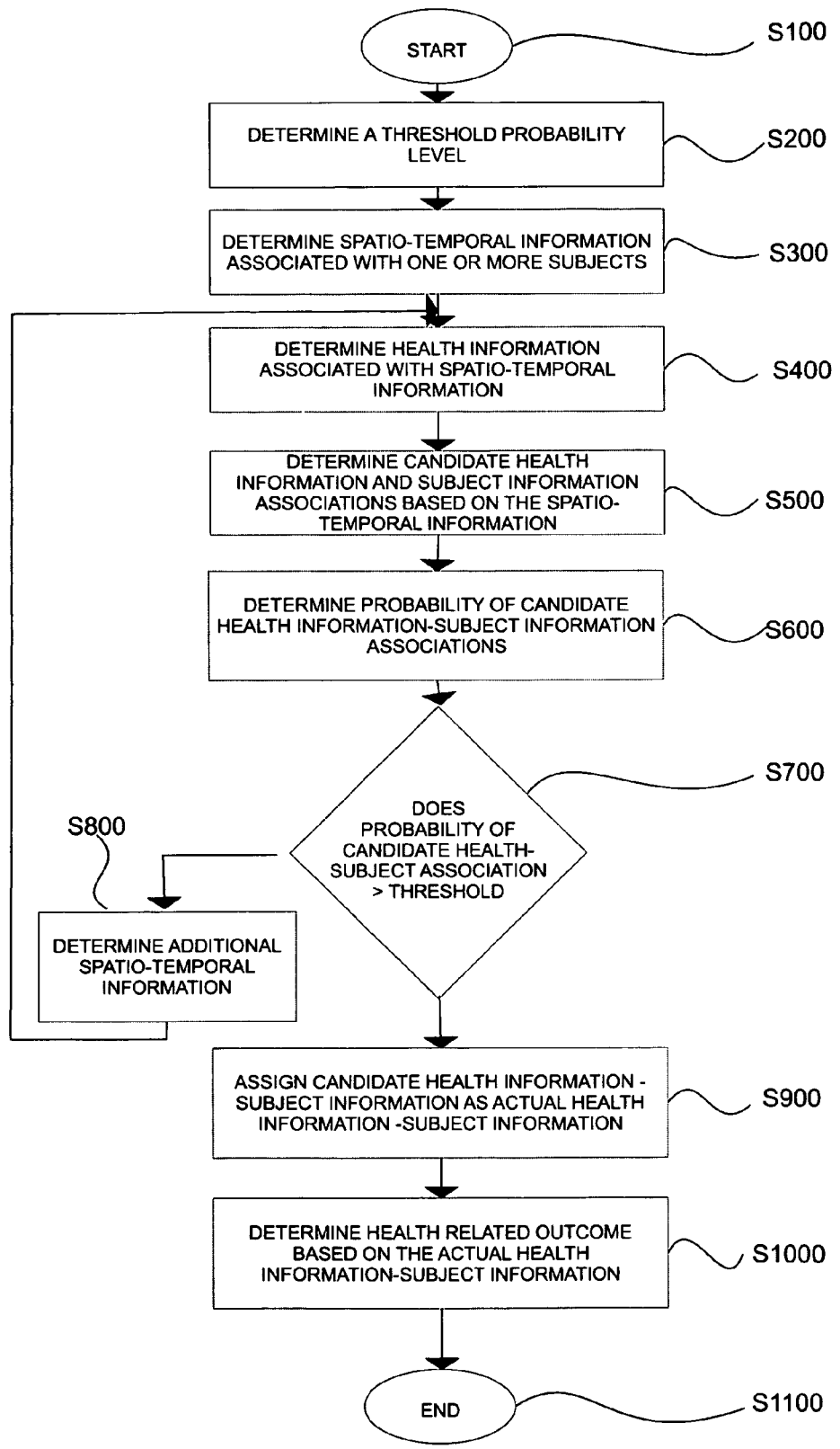
FIG. 2 is an exemplary flowchart of a method for dynamically determining data-identity associations according to this invention.

FIG. 2 is an exemplary flowchart of a method for dynamically determining data-identity associations according to this invention. The process begins at step S100 and immediately continues to step S200.

In step S200, a threshold probability level is determined. The threshold probability level specifies the minimum probability level required for an inferred health information—subject information association to be considered valid or correct. In one exemplary embodiment, the identity of a subject is registered. For example, in various embodiments according to this invention, registration is accomplished via manual enrollment at an entry point, via a carried RFID tag or other token, biometrics and/or the like. Unknown users are tagged as others. Unknown or other users may be prompted to register their identity at later times. In various exemplary embodiments according to this invention a threshold probability level may be associated with information based on the type or criticality of the information. After the threshold probability level has been determined, control continues to step S300.

Spatio-temporal information associated with one or more subjects is determined in step S300. For example, in one exemplary embodiment, location sensors are used to determine when subjects pass from the bedroom through a hallway to the bathroom. Further information is gathered when the subject moves from the bathroom into the hallway and then moves into the kitchen. In some embodiments, the sensors are comprised of cameras. These camera sensors compare features of the sensed image to known subject profiles to infer identity. In other cases, personalized alarm or entry/exit codes are used to label the path or trajectory of the user. In various other exemplary embodiments, built-in or learned models of variance are used, assisting the association process by specifying how information from a sensor and/or information about a user characteristic can vary over time.

For example, a user characteristics such as weight may be associated with a variance of a 1.1 pounds or 0.5 kilograms per day for a first user and 2.2 pounds or 1 kilogram per day for a second user, allowing the system to calculate the probabilities that a particular sensor reading is an updated value of a previous measurement taken a know number of days in the past. In various other embodiments, the variance models determine different variance values over time. In still other embodiments, the uncertainty associated with measured sensor values is returned and used in the determinations of the acceptable variance. After the spatio-temporal information has been determined, control continues to step S400.

In step S400, spatio-temporally tagged health information is determined. In various embodiments, the spatio-temporally tagged health information includes the results of blood pressure tests, weight readings, blood glucose monitoring, urine analysis and/or other types of tests. For example, glucose, temperature and/or urine based may be determined using automated toilet monitoring systems such as the Matsushita's "Smart Toilet". After the spatio-temporally tagged health information is determined, control continues to step S500.

The candidate health information—subject information associations are determined in step S500. That is, for each health test, candidate subjects associated with the test are identified by assigning a probability to the N-most likely subjects. The various types of location and identification information are used in conjunction with historical health sensor values to resolve otherwise ambiguous information. Control then continues to step S600.

In step S600, probabilities for the candidate health-subject information association are determined. Thus, as additional information becomes available about a subject, the subject's identity may become apparent as reflected in the health-subject association probability scores. In some exemplary embodiments, a map of the monitored area is combined with the order, position and time at which the various sensors are triggered. After the probabilities have been determined, control continues to step S700.

In step S700, a determination is made as to whether the probability of candidate health-subject association is greater than the threshold. If it is determined that the probability of the candidate health-subject association is less than the threshold, control continues to step S800. In step S800, additional spatio-temporal information is determined. Control then jumps to step S400. Steps S400-S800 are then repeated until probability of the candidate health-subject information exceed the threshold. Control then continues to step S900.

The candidate health information-subject information is assigned as the actual health information-subject information in step S900. Control then continues to step S1000. Health related outcomes are determined based on the actual health information-subject information. Control then continues to step S1100 and the process ends.

Figure 3:
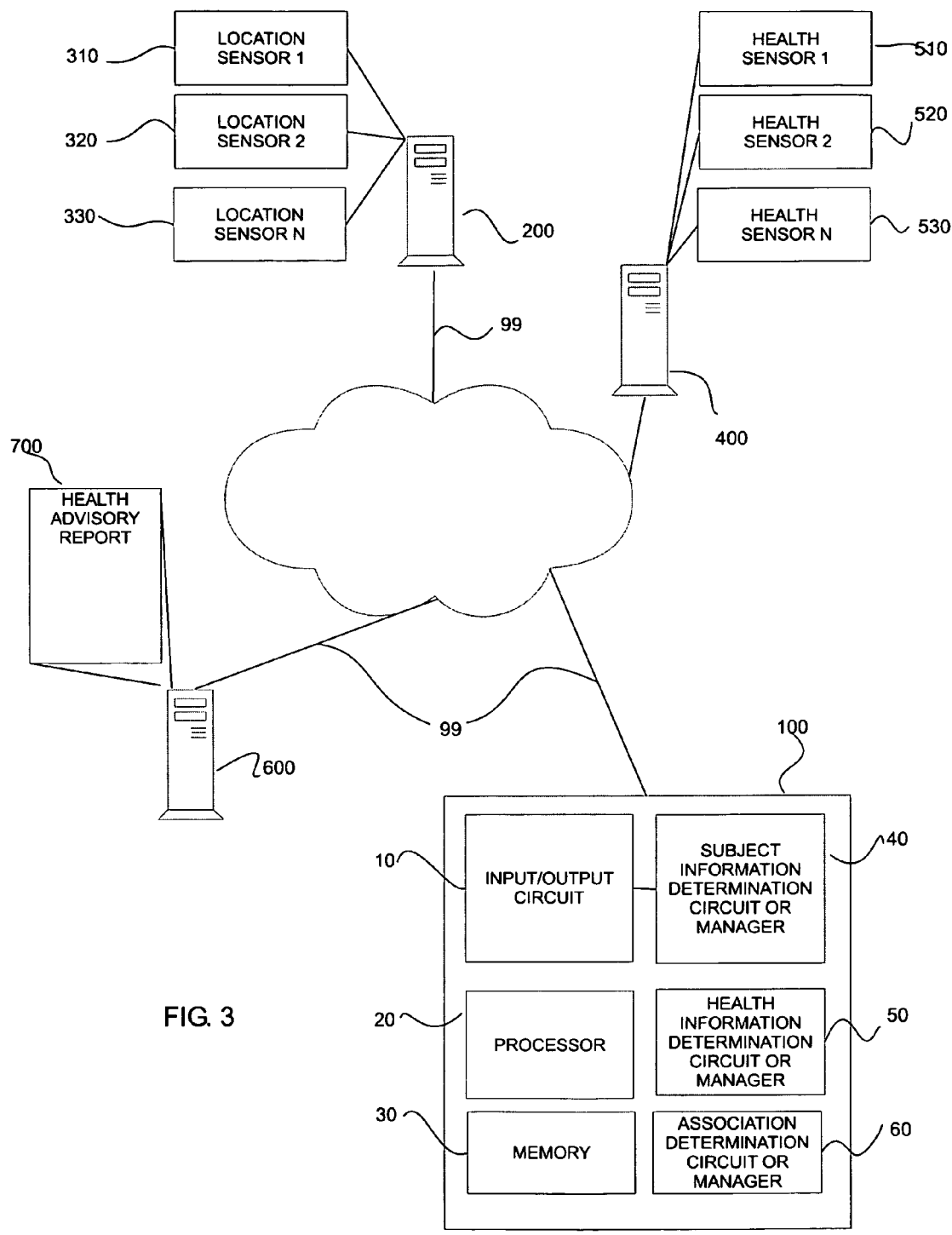
FIG. 3 is an exemplary system for dynamically determining association-data according to this invention.

FIG. 3 is an exemplary system for dynamically determining data-identity associations 100 according to this invention. The system for dynamically determining data-identity associations 100 is connected via communications links 99 to a location/identity server 200, a health information server 400 and to a health monitoring server 600.

The input/output circuit 10 of the system for dynamically determining data-identity associations 100 is activated to retrieve location and identity information from location and identity sensors 1-N, 310-330 via the location/identity server 200 and the health information server 400. However, it will be apparent that in various other embodiments, the information can also be retrieved directly form the location/identity sensors 1-N, 310-330. The processor 20 then stores the location/identity information in memory 30 and activates the subject information determination circuit or manager 40.

The subject information determination circuit or manager 40 determines subject paths through the monitored area. For example, a subject passing through a monitored area may trigger several different sensors. One or more of the sensors, such as an electronic entry key terminal or the like may be used to associate the path with specific known users to form identity tagged spatio-temporal information.

The processor 20 then activates the health information determination circuit or manager 50 to determine health information associated with spatio-temporal information. For example, in various embodiments, weight readings are retrieved from the health sensors 1-N, 510-530. by the health information server 400 and stored in memory 30. The health information determination circuit or manager 50 associates the weight health information with the spatio-temporal information to form spatio-temporally tagged health information. In various exemplary embodiments, built-in or learned variance models describe how the information from the sensors varies over time. Thus a weight measurement might be associated with a variance over a specific time interval such as days, weeks, months or like or may dynamically vary over periods of time. This allows the system to make high-probability data-identity associations based on the variances associated with growing children, weight loss and the like.

In one exemplary embodiment, a full-grown adult's height measurement is associated with a smaller variances than the variance for a growing child. In still other embodiments, sensors such as an exemplary height sensor provide or return information about the uncertainty associated with a measurement. The uncertainty is then used determine the significance to be accorded to any detected changes.

The processor 20 then activates the association determination circuit or manager 60. The association determination circuit or manager 60 determines candidate health-subject associations for the health information. In various embodiments, the health-subject associations are scored. While the probability score of the association is less than a determined threshold, additional spatio-temporally tagged identity and/or health information is used to further adjust the scores until the threshold is exceeded. Once the threshold is exceeded, a health-subject association is created. The health-subject information association is then used to create a report, select procedures or the like. It will be apparent that in various other embodiments, different types of information may be associated with varying thresholds without departing from the spirit or scope of this invention. In some embodiments, the order, timing and position of triggered or activated sensors is exploited to determine the identity of a subject.

In still other exemplary embodiments, specific current health sensor readings are correlated with the prior health sensor readings of users known to the system. This information can also be used to further refine the scoring model associating the health information with specific known users based on the spatio-temporal information and the health sensor values.

FIG. 4 is an exemplary data structure for storing spatio-temporal information according to an aspect of this invention. The exemplary data structure for storing spatio-temporal information is comprised of a sensor identifier portion 810, a location portion, 820, a time portion 830, and a sensor description portion 840.

The first row of the data structure contains the value "AB36" in the sensor identifier portion 810. The value "AB36" uniquely identifies the sensor within the network. The location portion 820 contains the value "BEDROOM" indicating that the sensor is located in the bedroom. However, it will be apparent that various other means of describing the location of the sensors may also be used without departing from the scope of this invention.

The time portion 830 contains the value "10:40". This temporal value indicates the time when the sensor was activated. The path of a subject through the monitored area is likely to trigger a plurality of sensors. The determined sensor values can be used to disambiguate the identity of the subject. Thus, if two known subjects or users are known to be in the master bedroom and each subject differs in height and weight. Height and weight sensors placed in the bathroom and/or other locations can be used to infer the identity of the subjects. Thus, health readings proximally located in the subject's path through the monitored area can be automatically associated with the relevant subject.

The sensor description portion 840 contains the value "OCCUPANCY" indicating the sensor is an occupancy sensor. Occupancy sensors may be based on radar, high frequency sound, pressure switches, cameras, infrared and/or any other type of sensor, useable alone or in combination to detect presence in a monitored space.

The second row of the data structure contains the value "AB50" in the sensor identifier portion 810. The value "AB50" uniquely identifies the sensor within the network. The location portion 820 contains the value "HALLWAY1" indicating the location of the sensor within the monitored area. The time portion 830 contains the value "10:41". The temporal information indicates the time the sensor was activated. The sensor description portion 840 contains the value "SOUND" indicating the sensor monitors sound information via a microphone or the like.

The third row of the data structure contains the value "AB51" in the sensor identifier portion 810 uniquely identifying the sensor within the network. The location portion 820 contains the value "BATHROOM". The bathroom value indicates that the sensor is located in the bathroom. The time portion 830 contains the value "10:42" which indicates the time the sensor was activated. The sensor description portion 840 contains the value "HEIGHT" indicating the sensor is used to measure the height of a user and potentially infer the identity of the user.

The fourth row of the of the exemplary data structure for storing spatio-temporal information contains the values "AB52", "BATHROOM", "10:42" and "SOUND". The value "AB52" in the sensor identifier portion 810 uniquely identifies the sensor within the system. The "BATHROOM" value in the location portion 820 indicates the sensor is located in bathroom. It will be apparent that in various other exemplary embodiments according to this invention, multiple sensors may be placed in the same location without departing from the scope of this invention.

The value "10:42" in the time portion 830 indicates the time that the sensor was triggered. The "SOUND" value in the sensor description portion 840 indicates the sensor uses sound information. For example, in one exemplary embodiment, the sound based sensor "AB52" is a microphone based smart sensor that captures sounds associated with a subject's footsteps and uses the information to infer the identity of the subject.

The fifth row contains the values "AB50", "HALLWAY1", "10:48" and "SOUND". The sensor identifier portion 810 contains the value "AB50". This value identifies the sensor with the system. The location portion 820 contains the value "HALLWAY1" indicating that the sensor is located in the hallway1 portion of the monitored area. The time portion 830 contains the value "10:48" indicating the time when the subject activated or triggered the sensor. The sensor description portion 840 contains the value "SOUND" indicating that the sensor is a sound based sensor such as a microphone or the like.

The sixth row contains the value "AB54" in the sensor identifier portion 810. This value identifies the sensor within the system. The location portion 820 contains the value "KITCHEN" indicating that the sensor is located in the monitored area labeled "KITCHEN". The time portion 830 contains the value "10:48" corresponding to the time when sensor "AB54" was triggered or activated. The sensor description portion 840 contains the value "CAMERA" indicating a camera based sensor.

The seventh row contains the value "AB55" in the sensor identifier portion 810 identifying the sensor within the system. The location portion 820 contains the value "LIVING ROOM". Thus, sensor "AB55" is located within the monitored location associated with the label "LIVING ROOM". The time portion 830 contains the value "10:49" which is the time that sensor "AB55" was activated. The sensor description portion 840 contains the value "CAMERA" indicating the sensor is a camera based sensor.

The eighth row contains the value "AB56" in the sensor identifier portion 810 identifying the sensor within the system. The "FRONT DOOR" value in the location portion 820 indicates that the sensor is located at or near the monitored area labeled "FRONT DOOR". The time portion 830 contains the value 11:15 which is the time when sensor AB56 was activated. The sensor description portion 840 contains the value "ELECTRONIC KEY" indicating that the sensor is an electronic key device. In one exemplary embodiment according to this invention, each user is provided with distinct or unique electronic keys or codes. When the user of the electronic key device enters their token and/or code, fingerprint, iris scan or other information, an inference is made that the holder of the electronic key has been identified. Subsequent user data-identity associations can then be made based on the user paths detected by the various location sensors within the monitored area.

The ninth row of the data structure contains the value "AB57" in the sensor identifier portion 810 uniquely identifying the sensor within the system. The location portion 820 contains the value "BATHROOM" indicating the sensor is located in the bathroom. The time portion 830 contains the value "11:16" which indicates that the sensor was activated at 11:16. The sensor description portion 840 contains the value "SCALE". This indicates that the sensor is a weight scale sensor for determining the weight of a user. It will be apparent that weight is a characteristic of a user that tends to change slowly over time. Thus, if each subject is associated with different weights, the value of the scale can be used to adjust the score of any proposed data-identity association.

The tenth row contains the value "AB58" in the sensor identifier portion 810 indicating the unique identifier of the sensor with the system. The value "FRONT DOOR" in the location portion 820 indicates the sensor the sensor location at the front door. The value "11:15" in the time portion 830 indicates the time when the front door sensor was activated. The sensor description portion 840 contains the value "PRESSURE MAT" indicating that the sensor is a pressure mat able to take weight readings of subjects.

In various exemplary embodiments, the pressure mat readings are compared with the electronic key information obtained from the electronic key sensor described above. Various protocols or procedures can be implemented. For example, if the subject is identified as a guest, then a weight reading is taken and assigned to guest1. Other weight sensors can then be used to tag the guest subject's path within the monitored area or environment based on the weight information even without more specific identification of the subject. This will also enhance the accuracy of data-identity association for registered non-guest users.

In other exemplary embodiments according to this invention, the weight of subjects identified or tagged by the electronic key are compared to historical weight information. The information can be used to identify possible attempts to masquerade as the holder of the electronic key. In cases of weight loss over extended periods, a recalibration procedure may be triggered. The recalibration system may use other user characteristics such as a palm vein reader—such as the Fujitsu contact-less palm vein authentication device, an iris or retina scanner, a fingerprint scanner, a voice print recognition device, a camera recognizer, a typed password and the like, either alone or in combination.

The last row contains the value "AB77" in the sensor identifier portion 810 which identifies the sensor within the system. The location portion 820 contains the value "LIVING ROOM". This value indicates that sensor "AB77" monitors the "LIVING ROOM" area. The time portion 830 contains the value "10:00 indicating the time the sensor was activated or triggered by a subject. The sensor description portion 840 contains the value "CAMERA" indicating that the sensor is a camera type of sensor.

FIG. 5 is an exemplary data structure for storing spatio-temporal health information 900 according to an aspect of this invention. The exemplary data structure for storing spatio-temporal health information 900 is comprised of a sensor identifier portion 910, a location portion 920, a time portion 930 and a description portion 940.

The first row of the exemplary data structure for storing spatio-temporal health information 900 contains the value "AB46" in the sensor identifier portion. This value identifies the sensor within the system. It will be apparent that various methods of sensor identification may be used without departing from the spirit or scope of this invention.

The location portion 930 contains the value "BATHROOM". This value indicates the location of the sensor within the monitored area. In this case, the sensor is located within the monitored area identified by the label "BATHROOM". The time portion 930 contains the value "10:43" indicating when the sensor was activated or triggered. The description portion 940 contains the value "GLUCOSE MONITOR" which describes the type of health sensor associated with the sensor identifier "AB46".

The second row of the exemplary data structure for storing spatio-temporal health information 900 contains the value "AB46". This indicates that the data in the second row is derived from the same sensor as the information in the first row. The location portion 920 contains the value "BATHROOM" identifying the location of the sensor within the monitored area. The time portion 930 contains the value "12:03" indicating the time at which the sensor information was obtained. The description portion 940 contains the value "GLUCOSE MONITOR" indicating the type of sensor. The time and location information from the user paths within the monitored area and the actual glucose level values retrieved from the glucose monitor can be used to infer an association with a specific user.

The third row contains the value "AB46" in the sensor identifier portion 910. The location portion 920 contains the value "BATHROOM" indicating the location within the monitored area. The time portion contains the value "15:04" as the time when the sensor was activated. The description portion contains the value "GLUCOSE MONITOR" indicating the sensor is a glucose monitoring sensor.

The fourth row contains the value "AB46" in the sensor identifier portion 910. The location portion 920 contains the value "BATHROOM" indicating the location within the monitored area. The time portion contains the value "23:18"

as the time when the sensor was activated. The description portion contains the value "GLUCOSE MONITOR" indicating the sensor is a glucose monitoring sensor. The The fifth row contains the value "AB97" in the sensor identifier portion 910. The location portion 920 contains the value "KITCHEN" indicating the location of the sensor within the monitored area. The time portion contains the value "10:49" as the time when the sensor was activated. The description portion contains the value "BLOOD PRESSURE MONITOR" indicating the sensor is a blood pressure type monitoring sensor.

The sixth row contains the value "AB97" in the sensor identifier portion 910. The location portion 920 contains the value "KITCHEN" indicating the location within the monitored area. The time portion contains the value "12:03" as the time when the sensor was activated. The description portion contains the value "BLOOD PRESSURE MONITOR" indicating the sensor is a blood pressure monitoring sensor.

The seventh row contains the value "AB97" in the sensor identifier portion 910. The location portion 920 contains the value "KITCHEN" indicating the location within the monitored area. The time portion contains the value "12:15" as the time when the sensor was activated. The description portion contains the value "BLOOD PRESSURE MONITOR" indicating the sensor is a blood pressure monitoring sensor.

The eighth row contains the value "AB97" in the sensor identifier portion 910. The location portion 920 contains the value "KITCHEN" indicating the location within the monitored area. The time portion contains the value "23:01" as the time when the sensor was activated. The description portion contains the value "BLOOD PRESSURE MONITOR" indicating the sensor is a blood pressure monitoring sensor.

The ninth row contains the value "AB57" in the sensor identifier portion 910. The location portion 920 contains the value "BATHROOM" indicating the sensor is located within the bathroom. The time portion contains the value "11:16" as the time when the sensor was activated. The description portion contains the value "SCALE" indicating a weight sensor.

The tenth row contains the value "AB58" in the sensor identifier portion 910. The location portion 920 contains the value "FRONT DOOR" to indicate that the sensor is located at the front door within the monitored area. The time portion contains the value "11:15" indicating the time the sensor was activated. The description portion contains the value "PRESSURE MAT" indicating the sensor is a pressure type of weight sensor.

The last row contains the value "AB71" in the sensor identifier portion 910. The location portion 920 contains the value "LIVING ROOM" indicating its position within the monitored area. The time portion contains the value "10:00" as the time of activation. The description portion contains the value "TEMPERATURE MONITOR" indicating the sensor is a temperature monitoring sensor.

FIG. 6 is an exemplary data structure for storing historical health sensor information 1000 according to an aspect of this invention. The exemplary data structure for storing historical health sensor information 1000 is comprised of a sensor identifier portion 1010, a time portion 1020 and a reading or value portion 1030.

The first row contains the value "AB46" in the sensor identifier portion 1010. In one exemplary embodiment, sensor "AB46" is identified as a glucose monitor located in the "BATHROOM" area. The time portion 1020 contains the value "10:43" indicating the time the sensor was triggered or activated. The value portion 1030 contains the value "10" indicating the sensor reading or value.

The second row contains the value "AB46" in the sensor identifier portion 1010 indicating that the data was collected by the same glucose monitor sensor. The time portion 1020 indicates the data was collected at 12:03. Thus, the data could be from the same subject later in the day or could be from a different subject. The reading portion 1030 contains the value "15". In various exemplary embodiments, the paths of users or subjects within the monitored area are monitored over time. The accumulated spatio-temporal identity information is used to adjust the confidence levels associated for subject-health information associations.

The third row contains the value "AB46" in the sensor identifier portion 1010. The time portion 1020 contains the value "15:04" indicating the time when the sensor was activated or triggered. The reading portion 1030 contains the value "12". In various other exemplary embodiments according to this invention, the reading portion value for relatively stable features such as weight, height or the like are used to adjust confidence scores associating the value with specific users within the monitored area.

The fourth row contains the value "AB46" in the sensor identifier portion 1010. The time portion 1020 contains the value "23:18" indicating the trigger time of the sensor. The reading portion 1030 contains the value "13" indicating the glucose level.

The fifth row contains the value "AB97" in the sensor identifier portion 1010. This value is associated with a blood pressure monitor located in the "KITCHEN" area. The time portion contains the value "10:48" indicating when the blood pressure monitoring sensor was activated. The reading portion 1030 contains the value 180/90 indicating the value of blood pressure readings obtained from the sensor.

The sixth row contains the value "AB97" in the sensor identifier portion 1010 and is associated with the blood pressure monitor located in the "KITCHEN" area. The time portion contains the value "12:03" indicates the activation time. The reading portion 1030 contains the value 180/92 indicating the value of blood pressure readings obtained from the sensor. The readings are close in value to the readings obtained at 10:48.

The seventh row contains the value "AB97" in the sensor identifier portion 1010 and is associated with the blood pressure monitor located in the "KITCHEN" area. The time portion contains the value "12:15" indicates the activation time of the sensor. The reading portion 1030 contains the value 110/90 obtained from the blood pressure sensor. The readings are not close in value in to the readings obtained at 10:48 or 12:03. The spatio-temporal identity and health information is used to infer the probability of that the readings are associated with the same subject or user as the 10:48 or 12:03 readings.

The eighth row contains the value "AB97" in the sensor identifier portion 1010 and is associated with the blood pressure monitor located in the "KITCHEN" area. The time portion contains the value "23:01" indicates the activation time. The reading portion 1030 contains the value 110/90 which are close in value in to the readings obtained at 12:15. The spatio-temporal tagged identity and health information are used to determine a probability that the readings are associated with the same subject or user as the 10:48 or 12:03 readings.

The ninth row contains the value "AB57" in the sensor identifier portion 1010 which uniquely identifies the sensor within the system. The time portion 1020 contains the value "11:16" indicating the time when the sensor was activated. The readings portion 1030 contains the value "160" indicating the weight of the subject. By comparing the readings value to the weights associated with known users of the system, candidate health-subject association scores may be determined and/or adjusted since the weight characteristics fluctuate less over time. In this case, the reading value of "160" is consistent with user #1 as indicated in line 2 of FIG. 7 but inconsistent with user #2 as indicated by the last line of FIG. 7. Thus, the score for user #1 is increased and the score for user #2 is decreased.

The tenth row contains the value "AB58" in the sensor identifier portion 1010 which uniquely identifies the sensor within the system. The time portion 1020 contains the value "1:15" indicating the time when the sensor was activated. The readings portion 1030 contains the value "105" indicating the weight of the subject which is consistent with weight of user #2 but inconsistent with the weight of user #1. Thus, the score for user #1 is decreased and the score for user #2 is increased. It will be apparent that these probability adjustments assume that the user is a known user which may be determined based on the electronic key readings.

The last row contains the value "AB71" in the sensor identifier portion 1010. This sensor is a temperature sensor located in the living room. The time portion 1020 contains the value "10:00" as the time when the temperature was taken. The reading portion 1030 contains the value 98.9 as the temperature of the subject at the time.

FIG. 7 is an exemplary data structure for storing historical subject location information 1100 according to an aspect of this invention. The exemplary data structure for storing historical subject location information 1100 is comprised of a sensor identifier portion 1110; a time portion 1130; and a reading portion 1140.

The first row contains the value "AB36" in the identifier portion 1110. This value identifies the sensor with the system. The value of "10:40" in the time portion 1130 specifies the time when the reading was taken. The reading portion 1140 contains the value "OCCUPANCY=>TRUE" indicating that the monitored area is occupied. In various embodiments, the sensor is smart sensor that determines the occupancy based on multiple criteria such as motion sensing, infra-red and the like.

The second row contains the values "AB50", "10:41", "GAIT=>USER[1]". These values indicate that sensor AB50 identified user 1 based on the audio pattern of the user's gait at 10:41.

The third row contains the values "AB51", "10:42", "HEIGHT=>USER[1]". These values indicate that sensor AB51 identified user 1 based on a match between the user height characteristic and the height value returned by the sensor at 10:42.

The fourth row contains the values "AB52", "10:42", "OCCUPANCY=>TRUE" indicating that sensor AB52 has determined that area monitored by sensor AB52 was occupied at 10:42.

The fifth row contains the values "AB50", "10:48", "GAIT=>USER[1]". These values indicate that sensor AB50 identified user 1 based on the audio pattern of the user's gait at 10:48.

The sixth and seventh rows contain values indicating that the sensor AB54 identified user 1 based on the video outline of a user at 10:48 and 10:49. The eighth row value indicates that the security exit code for user 1 was entered. The ninth row contains values indicating that the measured weight returned by the bathroom weight scale indicates user 2. The tenth row indicates that the measured weight returned by the pressure mat indicates user 1. Finally the last row indicates that the video outline returned by sensor AB77 indicates user 7 triggered the sensor.

FIG. 8 is an exemplary data structure for storing user information 1200 according to an aspect of this invention. The exemplary data structure for storing user information contains a user characteristics portion 1210.

The first row of the exemplary data structure for storing user information 1200 contains the value "user[1].height=6; ". This value indicates the user's height in feet. When a subject passes a height sensor, the reading from the height sensor can be used to determine if the subject is user "1" based on a comparison of the sensor information to the stored user height characteristic.

The second row contains the value "user[1].weight". This value indicates the weight of user "1". When the user uses the scales to measure their weight, the sensor readings may, in some case be used alone or in conjunction with other sensor information to infer an association to user "1".

The third row contains the value "user[1].sound.gait=ftp://ftp.abc.com/gait.dat". This value indicates that the pattern of the gait of user "1" is contained in the specified file accessible via ftp. The sound pattern can be used by one or more smart microphone based sensors to infer the identity of a user based on sound patterns or features associated with their gait.

In one exemplary embodiment, the sound pattern is downloaded from an ftp server. However, it will be apparent that the sound patterns or other information may be pre-determined or pre-loaded, read from storage within the system or across a network, read from a database and/or retrieved from any known or later developed information repository without departing from the spirit or scope of this invention. It will also be apparent that "http:" and/or various other known or later developed file transfer protocols may also be used in the practice of this invention.

The fourth row contains the value "user[1].sound.voice=ftp://ftp.abc.com/voice.dat". This value indicates the location of a voice model associated with user "1". In various embodiments, the voice model is used to infer and/or help adjust an inference of identity based on information obtained from a microphone or other sound based sensor.

The fifth row contains the value "user[1].video.top=ftp://ftp.abc.com/video_top.dat". This value indicates the location of a video based recognition model for user "1" based on features extracted from an image drawn from a ceiling-mounted camera or the like.

The sixth row contains the value "user[1].video.left=ftp://ftp.abc.com/video_left.dat". This value indicates the location of a video based recognition model for user "1" based on features extracted from a left hand side view of the user.

The seventh row contains the value "user[1].video.right=ftp://ftp.abc.com/video_right.dat". This value indicates the location of a video based recognition model for user "1" based on features extracted from a right hand side view of the user.

The eighth row contains the value "user[1].health.glucose=100. This indicates a normal glucose level for user[1]. Thus, levels significantly outside this level are less likely to be associated with user "1" and are more likely associated with other potential users within the monitored area.

The ninth row contains the value "user[1].health.temperature=98.6". This reflects the last temperature reading for user "1".

The tenth row contains the value "user[2].height=5.5". This indicates that users "1" and "2" differ in height. Thus, the height sensor can be used to help label and clarify which user is associated with given sensor readings.

The last row contains the value "user[2].weight=105". This indicates that user "2" is considerably lighter than user "1" and provides another sensor measurement that can be used to label user paths or traversals within the monitored area.

FIG. 9 is an exemplary data structure for storing variance models 1300 according to an aspect of this invention. The first row of the exemplary data structure for storing variance models 1300 contains the value "user[1].height. variance.value=1". This indicates that the height characteristic for user 1 can vary by 1 inch. The second row contains the value "user[1].height. variance.interval=30 indicating the variance may occur over 30 days. This allows the system to handle small incremental changes over time without requiring explicit updates or re-calibration. In general, the variance model of a specific measurement depends on the characteristics of the subject (e.g. how it may change over time, space and activities) and the characteristics of the measurement device/method (e.g., what kind of measurement uncertainty is inherent in the device/method). Thus, it will be apparent that a variety of probabilistic models may be used for describing the characteristics of the subject and the device/method without departing from the scope of this invention.

The third and fourth rows contain the values "user[1].weight.variance=1" and "user[1].weight.interval=30" indicating that the measured weight of user 1 may vary by up to 1 pound over a 30 day interval without requiring an explicit re-calibration and re-authentication of the measured features.

The last two rows contain the values "user[2].height.variance=0.5" and "user[2].height.interval=30" indicating that the measured height of user 2 may vary by up to a one half pound over a 30 day interval without requiring an explicit re-calibration and re-authentication of the measured features.

In the various embodiments of the system for dynamically determining data-identity associations 100, each of the circuits 10-60 outlined above can be implemented as portions of a suitably programmed general-purpose computer. Alternatively, 10-60 of the system for dynamically determining data-identity associations 100 outlined above can be implemented as physically distinct hardware circuits within an ASIC, or using a FPGA, a PDL, a PLA or a PAL, or using discrete logic elements or discrete circuit elements. The particular form each of the circuits 10-60 of the system for dynamically determining data-identity associations 100 outlined above will take is a design choice and will be obvious and predictable to those skilled in the art.

Moreover, the system for dynamically determining data-identity associations 100 and/or each of the various circuits discussed above can each be implemented as software routines, managers or objects executing on a programmed general purpose computer, a special purpose computer, a microprocessor or the like. In this case, the system for dynamically determining data-identity associations 100 and/or each of the various circuits discussed above can each be implemented as one or more routines embedded in the communications network, as a resource residing on a server, or the like. The system for dynamically determining data-identity associations 100 and the various circuits discussed above can also be implemented by physically incorporating the system for dynamically determining data-identity associations 100 into software and/or hardware system, such as the hardware and software systems of a web server or a client device.

As shown in FIG. 3, memory 30 can be implemented using any appropriate combination of alterable, volatile or non-volatile memory or non-alterable, or fixed memory. The alterable memory, whether volatile or non-volatile, can be implemented using any one or more of static or dynamic RAM, a floppy disk and disk drive, a write-able or rewrite-able optical disk and disk drive, a hard drive, flash memory or the like. Similarly, the non-alterable or fixed memory can be implemented using any one or more of ROM, PROM, EPROM, EEPROM, an optical ROM disk, such as a CD-ROM or DVD-ROM disk, and disk drive or the like.

The communication links 99 shown in FIGS. 1 & 3, can each be any known or later developed device or system for connecting a communication device to the system for dynamically determining data-identity associations 100, including a direct cable connection, a connection over a wide area network or a local area network, a connection over an intranet, a connection over the Internet, or a connection over any other distributed processing network or system. In general, the communication links 99 can be any known or later developed connection system or structure usable to connect devices and facilitate communication and may use various data communication protocols without departing from the scope of this invention.

Further, it should be appreciated that the communication links 99 can be wired or wireless links to a network. The network can be a local area network, a wide area network, an intranet, the Internet, or any other distributed processing and storage network.

While this invention has been described in conjunction with the exemplary embodiments outlined above, it is evident that many alternatives, modifications and variations will be apparent to those skilled in the art. Accordingly, the exemplary embodiments of the invention, as set forth above, are intended to be illustrative, not limiting. Various changes may be made without departing from the spirit and scope of the invention.

It should be apparent that the term "variance model" as used in the text refers to both a model of change and a model of uncertainty. A model of change describes how a quantity will change over time, and a model of uncertainty describes the probability distribution of a specific quantity. For example, a person's weight could be expected to increase after a meal. The system may discover that the subject's weight, on average, increases 1 pound after breakfast, 1 pound after lunch and 2 pound after dinner. This is a simple example of food intake related conditional model of weight change. An example model of uncertainty is that while, the subject's weight increases 1 pound after lunch on average, the actual measurement result would range between 0.5 pound to 1.8 pound, with a corresponding probability for each possible value within the range.

What is claimed is:

1. A method for dynamically determining data-identity information comprising the steps of:
    determining, in a computer system, spatio-temporal information associated with at least one subject;
        wherein the spatio-temporal information is determined from multiple sensors; and
        wherein the spatio-temporal information is insufficient to identify a subject;
    determining, in the computer system, a mapping between identity information and the spatio-temporal information for at least one subject, wherein the determining is based on inferring the at least one subject's path or trajectory using tagged location information;
    determining, in the computer system, a mapping between health information and the spatio-temporal information;
    determining, in the computer system, probable mappings between the health information and the identity information based on the determined mapping between the spatio-temporal information and the identity information, as well as the determined mapping between the health information and the spatio-temporal information;
    determining mappings between the health information and the identity information from the probable mappings, wherein ambiguity in the determination is resolved using additional spatio-temporal, identity, and health information;
and
determining, in the computer system, health related procedures based on the determined mappings between the health information and the identity information.

2. The method of claim 1, in which the sensor information is at least one of video, sound, chemical, weight, and height based sensor information.

3. The method of claim 1 where health information is based on at least one of cardio-vascular information, body fluids and video information.

4. The method of claim 1, in which identity information is based on at least one of: a code, historical sensor information and spatio-temporal information.

5. The method of claim 1, in which health information is based on at least one of: a code, historical sensor information and spatio-temporal information.

6. The method of claim 1, in which probable mappings are scored based on at least one of: the identity information and the health information.

7. The method of claim 6, in which probable mappings having a score that exceeds a threshold are explicitly associated and mappings with scores below the threshold are retained for later resolution.

8. The method of claim 6, in which the identity information is comprised of different types of information, and the health information is comprised of different types of information.

9. The method of claim 8, in which the different types of information comprising the identity information and the health information are associated with different thresholds.

10. The method of claim 1, further comprising the steps of:
determining variance models for at least one of: the identity information, the health information and the measurement method; and where the determining the probable mappings and identity information is further based on the variance models.

11. A system for dynamically determining data-identity information comprising:
a spatio-temporal information determination circuit for determining mappings between spatio-temporally tagged location information and subject-identity information,
wherein the spatio-temporal information is determined from multiple sensors;
wherein the spatio-temporal information is insufficient to identify a subject; and
wherein the mapping determination is based on inferring the at least one subject's path or trajectory using tagged location information
a health information determination circuit for determining spatio-temporally tagged health information;
a mapping determination circuit that establishes mappings between the health information and the identity information based on the mappings between the spatio-temporally tagged location information and subject-identity information, and the spatio-temporally tagged health information, wherein ambiguity in the determination is resolved using additional spatio-temporal location, identity, and health information; and
a processor that determines health related procedures based on the determined mappings between the health information and the subjects.

12. The system of claim 11, in which the sensor information is at least one of video, sound, chemical, weight, and height based sensor information.

13. The system of claim 11 where health information is based on at least one of cardio-vascular information, body fluids and video information.

14. The system of claim 11, in which identity information is based on at least one of: a code, historical sensor information and spatio-temporal information.

15. The system of claim 11, in which health information is based on at least one of: a code, historical sensor information and spatio-temporal information.

16. The system of claim 11, in which probable mappings are scored based on at least one of: the identity information and the health information.

17. The system of claim 16, in which probable mappings having a score that exceeds a threshold are explicitly associated.

18. The system of claim 16, in which the identity information is comprised of different types of information, and the health information is comprised of different types of information.

19. The system of claim 18, in which the different types of information comprising the identity information and the health information are associated with different thresholds.

20. The system of claim 11, in which the processor determines variance models for at least one of: the identity information the health information and the measurement method; and the probable mappings and identity information is further based on the variance models.

21. A tangible computer readable storage medium storing instructions that, when executed by a computer, cause the computer to perform a method for dynamically determining data-identity information, the method comprising:
determining spatio-temporal information associated with at least one subject;
wherein the spatio-temporal information is determined from multiple sensors; and
wherein the spatio-temporal information is insufficient to identify a subject;
determining a mapping between identity information and the spatio-temporal information for at least one subject, wherein the determining is based on inferring the at least one subject's path or trajectory using tagged location information;
determining a mapping between health information and the spatio-temporal information;
determining probable mappings between the health information and the identity information based on the determined mapping between the spatio-temporal information and the identity information, as well as the determined mapping between the health information and the spatio-temporal information;
determining mappings between the health information and the identity information from the probable mappings, wherein ambiguity in the determination is resolved using additional spatio-temporal, identity, and health information;
and
determining health related procedures based on the determined mappings between the health information and the identity information.

* * * * *